United States Patent [19]
Gilchrest et al.

[11] Patent Number: 5,580,547
[45] Date of Patent: Dec. 3, 1996

[54] STIMULATION OF TANNING BY DNA FRAGMENTS OR SINGLE-STRANDED DNA

[75] Inventors: Barbara A. Gilchrest, Brookline; Mina Yaar, Sharon; Mark Eller, Boston, all of Mass.

[73] Assignee: Trustees of Boston University, Boston, Mass.

[21] Appl. No.: 463,425

[22] Filed: May 26, 1995

Related U.S. Application Data

[62] Division of Ser. No. 88,251, Jul. 7, 1993, Pat. No. 5,470,577.
[51] Int. Cl.$^6$ .............................. A61K 37/22; A61K 9/50
[52] U.S. Cl. ........................... 424/59; 424/450; 424/520; 424/561; 514/43; 514/44; 514/788.1
[58] Field of Search ............................ 424/450, 59, 520, 424/561; 514/44, 43, 788.1

[56] References Cited

U.S. PATENT DOCUMENTS

| | | | |
|---|---|---|---|
| 3,937,809 | 2/1976 | Jacobi | 424/60 |
| 4,078,052 | 3/1978 | Papahadjopoulos | 514/44 |
| 4,419,343 | 12/1983 | Pauly | 424/59 |
| 4,866,038 | 9/1989 | Hruby et al. | 514/14 |
| 4,956,489 | 9/1990 | Auriol et al. | 560/40 |
| 5,135,917 | 8/1992 | Burch | 514/44 |
| 5,246,708 | 9/1993 | von Borstel et al. | 514/43 |
| 5,256,648 | 10/1993 | Gasparro et al. | 514/44 |
| 5,352,458 | 10/1994 | Yarosh | 424/450 |

FOREIGN PATENT DOCUMENTS

| | | |
|---|---|---|
| 0313446 | 10/1988 | European Pat. Off. . |
| 0318369 | 11/1988 | European Pat. Off. . |
| 0386680 | 3/1990 | European Pat. Off. . |
| 0416677A1 | 3/1991 | European Pat. Off. . |
| 0484199A1 | 5/1992 | European Pat. Off. . |
| 2511243 | 2/1983 | France . |
| 63-183518 | 7/1988 | Japan . |
| 63-301810 | 12/1988 | Japan . |
| WO91/07168 | 5/1991 | WIPO . |

OTHER PUBLICATIONS

Friedmann, P. S., et al., "Ultraviolet radiation directly induces pigment production by cultured human melanocytes", *J. Cell. Physiol.* 133(1):88–94 (1987).

Bonte, F., et al., "Kaempferol Liposome Activity on Skin Melanogenesis", *Congr. Int. Technol. Pharm.* 5th(3):404–407 (1989).

Niggli, H. J., et al., "Determination of Cytosine–Cytosine Photodimers in DNA of Cloudman S91 Melanoma Cells Using High Pressure Liquid Chromatography", *Photochem. & Photobiol.* 55(5):793–796 (1992).

Niggli, H. J., et al., "Sunlight–Induced Pyrimidine Dimers in Human Skin Fibroblasts in Comparison with Dimerization After Artificial UV–Irradiation", *Photochem. & Photobiol.* 48(3):353–356 (1988).

Niggli, H. J., et al., "Cyclobutane–Type Pyrimidine Photodimer Formation and Excision in Human Skin Fibroblasts After Irradiation With 313–nm Ultraviolet Light", *Biochem.* 22:1390–1395 (1983).

Niggli, H. J., "Comparative Studies on the Correlation Between Pyrimidine Dimer Formation and Tyrosinase Activity in Cloudman S91 Melanoma Cells After Ultraviolet–Irradiation", *Photochem. & Photobiol.* 52(3):519–524 (1990).

Niggli, H. J., et al., "Nucleosomal Distribution of Thymine Photodimers Following Far– and Near– Ultraviolet Irradiation", *Biochem. and Biophys. Research Communications* 105(3):1215–1223 (1982).

Sugitani, Yoshinori et al., "Red Shift in Photoacoustic Ultraviolet Absorption Spectra of Solid Purine Bases, Nucleosides and Nucleotides," *Analytical Sciences* 4:215–217 (1988).

Yaar, Mina and Gilchrest, Barbara A., "Human Melanocyte Growth and Differentiation: A Decade of New Data," *Journal for Investigative Dermatology, Inc.* 97(4):611–617 (1991).

Yarosh, Daniel B. et al., "Enhancement of DNA repair of UV damage in mouse and human skin by liposomes containing a DNA repair enzyme," *J. Soc. Cosmet. Chem.*, 41:85–92 (1990).

*Primary Examiner*—Nathan M. Nutter
*Attorney, Agent, or Firm*—Hamilton, Brook, Smith & Reynolds, P.C.

[57] ABSTRACT

A method of increasing pigmentation in mammalian skin, as well as protecting mammalian skin against ultraviolet damage, is disclosed. Also disclosed is a method of increasing pigmentation in mammalian cells, as well as a method of enhancing melanin production in mammalian melanocytes. A preparation useful in the present methods is additionally disclosed. The methods comprise administering to the epidermis or to the cells DNA fragments, either single- or double-stranded, or a mixture of both, or deoxynucleotides, in a liposomal preparation or other appropriate vehicle. The preparation includes DNA fragments or deoxynucleotides and an appropriate delivery vehicle, such as liposomes.

12 Claims, 4 Drawing Sheets

STIMULATION OF TANNING BY DNA FRAGMENTS OR SINGLE-STRANDED DNA

RELATED APPLICATION

This application is a division of application Ser. No. 08/088,251 filed Jul. 7, 1993, and now U.S. Pat. No. 5,470,577 which is incorporated herein by reference in its entirety.

FUNDING

Work described herein was funded in part by a grant from Christian Dior.

BACKGROUND

Human skin consists of two layers, the uppermost of which is the epidermis. The epidermis encompasses many different cell types, including melanocytes and keratinocytes. Melanocytes are specialized cells in the basal layer of the epidermis which synthesize melanin; the melanin is then packaged into melanosomes and then transported into keratinocytes.

It has been known for centuries that exposure of skin to the sun results in tanning, the skin's major form of endogenous protection against subsequent skin damage from ultraviolet (UV) irradiation. Melanin, a polymer which serves as a filter with absorbance within the UV range, provides photoprotection for the individual. The peak action spectrum for this phenomenon is in the UV-B range, 290–305 nm; various morphologic and enzymatic changes occur at the cellular level in epidermal melanocytes in response to UV irradiation. Proteins and nucleic acids of the epidermis absorb UV-B rays, causing the production of thymine dimers, which are known to be formed by UV irradiation of nuclear DNA and to be excised from the DNA strand by the action of highly specific enzymes, including endonucleases. If not removed, these dimers can stall DNA replication forks generating regions of single-stranded DNA. Failure to remove thymine dimers and other DNA mutations in the genome may lead to somatic mutations resulting in carcinogenesis.

In bacteria it is known that the DNA fragments released from stalled replication forks can interact with nuclear proteins which then regulate the expression of specific genes in the DNA as part of the organism's SOS response to UV damage. Bacteria do not tan, but tanning might reasonably be considered part of the analogous SOS response in mammalian skin. The precise stimulus for UV-induced tanning, however, remains unknown.

SUMMARY OF INVENTION

The current invention pertains to a method of increasing the pigmentation in skin. It consists of applying DNA fragments, either single- or double-stranded, or a mixture of both, or deoxynucleotides to the epidermis topically in a liposome preparation or other delivery vehicle, such that the fragments are available to cells of the epidermis and enter the nucleus of the melanocytes. This method results in the stimulation of a tanning response equivalent to that produced by sun exposure, but avoids subjecting the skin to the carcinogenic action of UV irradiation. The invention additionally pertains to a method of increasing pigmentation in melanocytes by applying DNA fragments, either single- or double-stranded, or a mixture of both, or deoxynucleotides to the cells such that the fragments or deoxynucleotides enter the nuclei of the melanocytes and increase melanin production. The invention also includes compositions useful in increasing pigmentation in skin, comprising DNA fragments or deoxynucleotides incorporated into liposomes or another delivery vehicle. Application of DNA fragments or deoxynucleotides by the method of the present invention results in a cosmetically pleasing tan that may also be protective against subsequent UV damage to the skin, including sunburn, photoaging, and development of skin cancer.

DETAILED DESCRIPTION OF THE INVENTION

Figure 1:
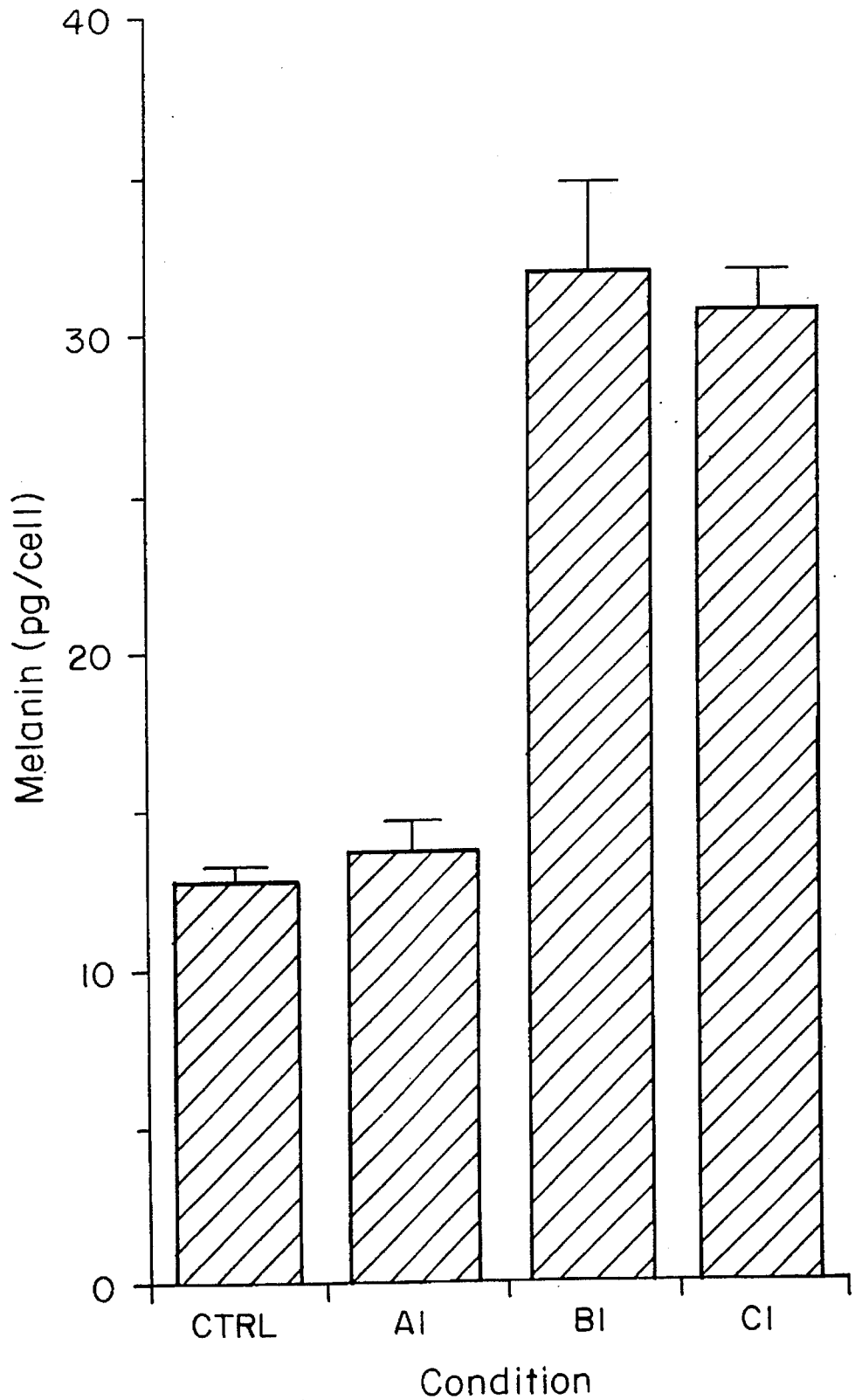
FIG. 1 is a graph depicting the effect on pigmentation of the exposure of S91 cells to DNA fragments in a phospholipid carrier. CTRL=control (no liposomes or DNA fragments); A1=empty liposomes (no DNA fragments); B1=liposomes containing UV-DNA (irradiated); C1=liposomes containing DNA (not irradiated).

The invention pertains to a method of increasing skin pigmentation or pigmentation in epidermal cells, particularly melanocytes, through the application of DNA fragments or deoxynucleotides, as well as to a preparation of DNA fragments or deoxynucleotides incorporated into a vehicle appropriate for application to mammalian epidermis or to mammalian cells.

In one method, DNA fragments, of approximately 2–200 bases in length, or deoxynucleotides (single bases), are administered topically to the epidermis, either in a liposome preparation or in another appropriate vehicle, such as propylene glycol, in a quantity sufficient to enhance melanin production. As used herein, "DNA fragments" refers to single-stranded DNA fragments, double-stranded DNA fragments, a mixture of both single- and double-stranded DNA fragments, or deoxynucleotides. "Deoxynucleotides" refers to either a single type of deoxynucleotide or a mixture of different deoxynucleotides. The DNA fragments or deoxynucleotides can come from any appropriate source. For example, salmon sperm DNA can be dissolved in water, and then the mixture can be autoclaved to fragment the DNA. The fragments can additionally be UV-irradiated. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used; the teachings of these patents are herein incorporated by reference. Alternatively, the DNA fragments or deoxynucleotides can be applied directly to the epidermis, or can be applied in any appropriate delivery vehicle. In addition, the DNA fragments or deoxynucleotides can be applied in a vehicle which specifically targets melanocytes. For example, a membrane marker specific for melanocytes, such as melanocyte stimulating hormone (MSH), can be incorporated into a liposome containing the DNA fragments or deoxynucleotides. The liposome preparation can also contain perfumes, colorants, stabilizers, sunscreens, diacyl glycerol or other ingredients. The preparation is applied topically to the skin surface once or twice daily for up to three weeks in a suitable vehicle at an effective concentration, which will generally be approximately 25–100 µM (or 0.05 to 10 mg/ml, depending on the molecular weight of the fragments employed).

A similar such method is used to increase pigmentation in mammalian cells, and particularly in melanocytes. In one embodiment, DNA fragments, either single- or double-stranded, or a mixture of both, or deoxynucleotides are applied to melanocytes in a liposome preparation or other appropriate vehicle, such as propylene glycol, under conditions such that the fragments enter the nuclei and melanin production is enhanced.

The invention is further illustrated by the following Exemplification.

EXEMPLIFICATION

Effect of DNA Fragments on the Pigmentation of S91 Cells

DNA for all experiments was fragmented salmon sperm DNA (Sigma Chemical Co.). Liposome preparations were obtained from Christian Dior.

In one experiment, S91 cells (a murine melanoma cell line) were plated at $2\times10^5$ cells per dish on 60 mm diameter culture dishes, in DME plus 10% calf serum (CS) at 37° C., and cultured for 24 hours (Day 1). On Day 2, the medium was changed, and cells were exposed to one of three additions: 100 µM empty liposomes ($A_1$); 100 µM liposomes containing UV-DNA (irradiated) ($B_1$); and 100 µM liposomes containing DNA (not irradiated) ($C_1$). The cells were then cultured for three days; on Day 5, the medium was changed and the cells were cultured for another three days in the presence of the respective additions. On Day 8 the cells were collected, and assayed for melanin.

The results of this experiment, as shown in FIG. 1, indicate that the addition of liposomes containing UV-DNA enhanced melanin production to a greater extent than the addition of empty liposomes or liposomes containing non-irradiated DNA; the addition of liposomes containing non-irradiated DNA enhanced melanin production in comparison to empty liposomes and the control.

In a second experiment, S91 cells were plated at $3\times10^5$ cells per dish on 60 mm culture dishes, in DME plus 10% CS at 37° C., and cultured for 24 hours (Day 1). On Day 2, the medium was changed, and cells were exposed to one of five additions: 100 µM empty liposomes ($A_1$); 100 µM liposomes containing UV-DNA (irradiated) ($B_1$); 100 µM liposomes containing DNA (not irradiated) ($C_1$); 100 µl (10 mg/ml) DNA (non-encapsulated (i.e. not within liposomes), and not irradiated); or 100 µl (10 mg/ml) DNA plus 10 minutes of UVC (non-encapsulated, and irradiated). The cells were then cultured for two days; on Day 4, the medium was changed and the cells were cultured for another three days in the presence of the respective additions. On Day 7 the cells were collected, and assayed for melanin.

Figure 2:
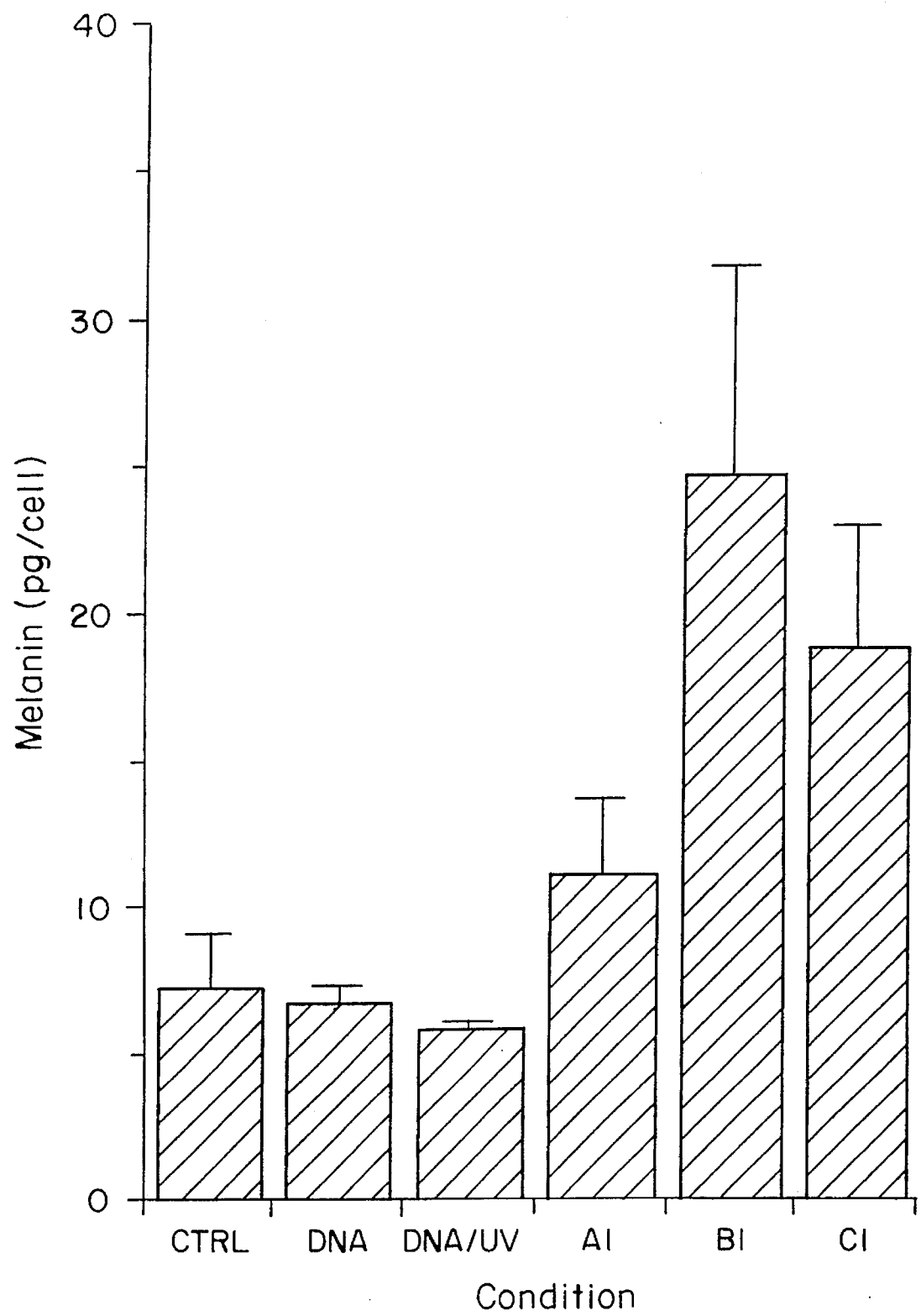
FIG. 2 is a graph depicting the effect on pigmentation of the exposure of S91 cells to DNA fragments. CTRL=control (no liposomes or DNA fragments); DNA=100 µl (10 mg/ml) DNA; DNA/UV=100 µl (10 mg/ml) DNA irradiated for 10 minutes with UVC; A1=empty liposomes (no DNA fragments); B1=liposomes containing UV-DNA (irradiated); C1=liposomes containing DNA (not irradiated).

The results of this experiment, as shown in FIG. 2, indicate that the addition of liposomes containing UV-DNA enhanced melanin production to a greater extent than the addition of empty liposomes, liposomes containing non-irradiated DNA, non-encapsulated DNA, or non-encapsulated UV-irradiated DNA. The addition of liposomes containing non-irradiated DNA enhanced melanin production to a greater extent than did the addition of empty liposomes, non-encapsulated DNA, or non-encapsulated UV-irradiated DNA.

Figure 3:
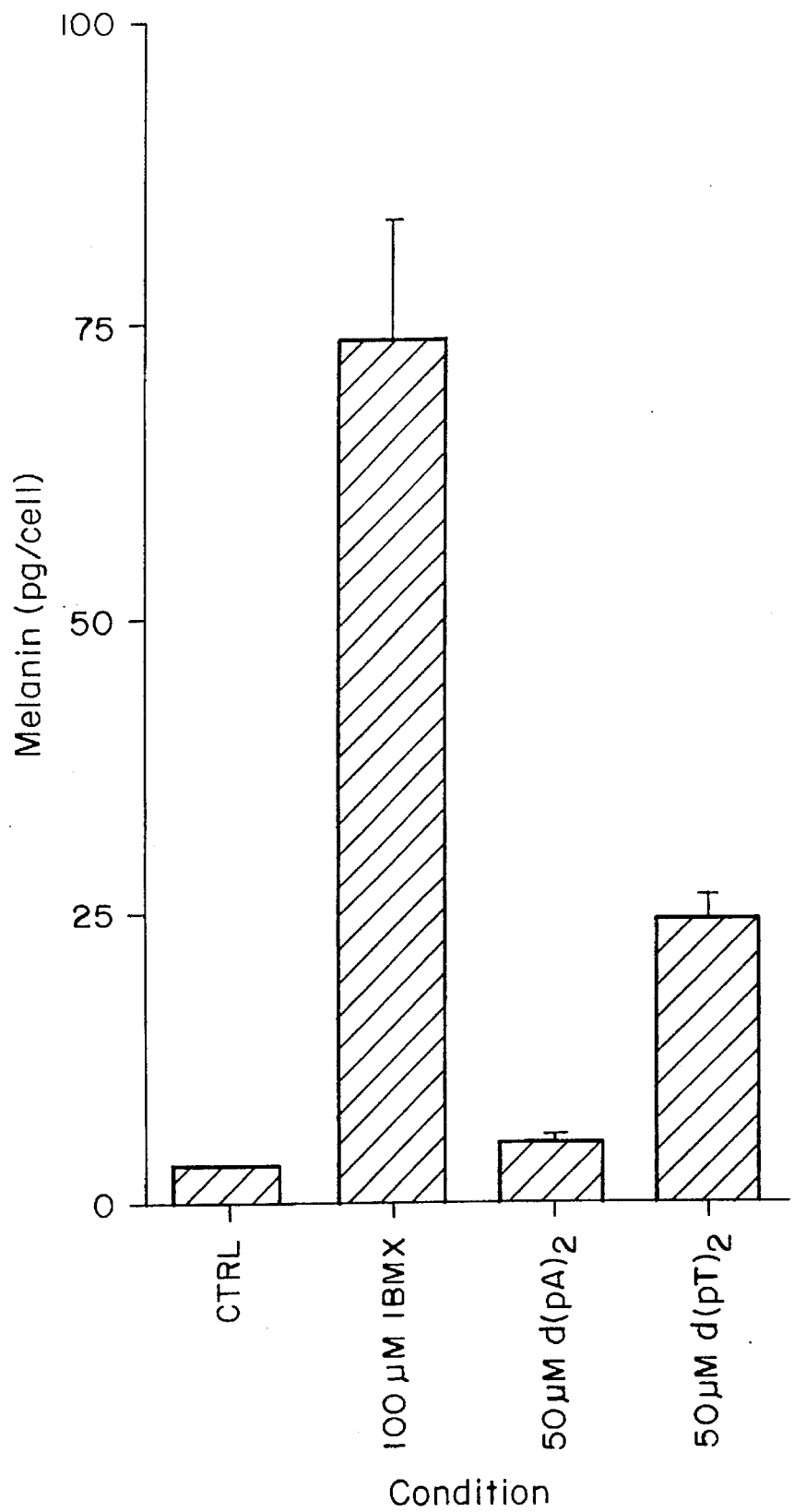
FIG. 3 is a graph depicting the effect on pigmentation of the exposure of S91 cells to the deoxydinucleotides $d(pT)_2$ and $d(pA)_2$, where $d(pA)_2$=deoxyadenylic acid dinucleotide and $d(pT)_2$=thymidylic acid dinucleotide. Control=no additions; 100 µM IBMX=isobutylmethylxanthine, a positive control.

In a third experiment, S91 cells were plated on 60 mm culture dishes in DME plus 10% calf serum (CS) at a density of $2\times10^5$ cells/dish. Two days later, the medium was changed and fresh DME plus 10% CS was added, along with either 50 µM deoxyadenylic acid dinucleotide ($d(pA)_2$), 50 µM thymidylic acid dinucleotide ($d(pT)_2$) or 100 µM isobutylmethylxanthine (IBMX), a known stimulator of melanogenesis in S91 cells, as a positive control. Four days later, the cells were collected and counted and an equal number of cells was pelleted for calculation of melanin/cell based on $OD_{475}$. FIG. 3 shows that while 50 µM $d(pA)_2$ yielded a 50% increase in melanin/cell compared to nontreated controls, $d(pT)_2$ gave a 7-fold increase. As is normally observed, IBMX stimulated pigmentation approximately 15-fold above background.

Figure 4:
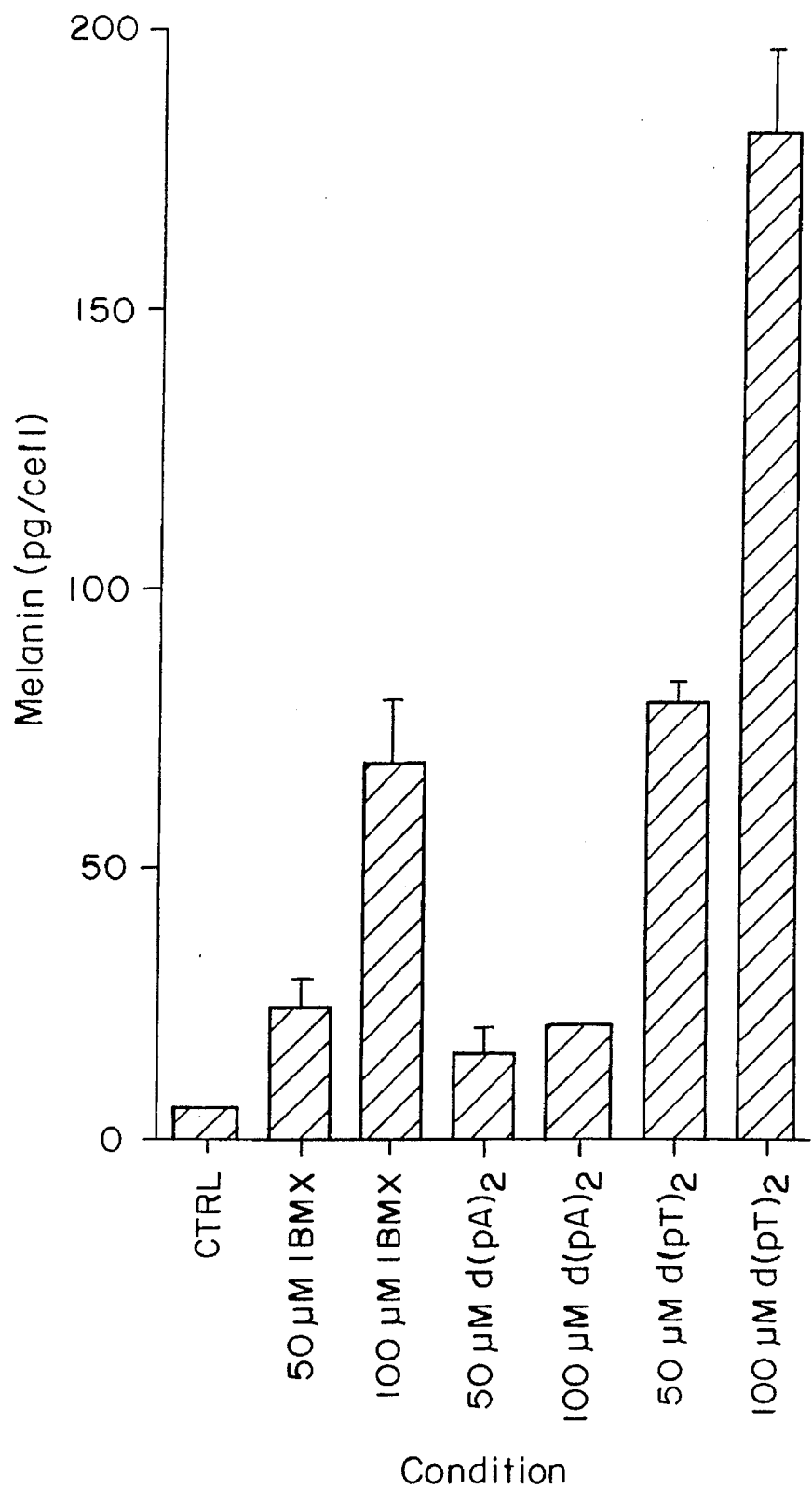
FIG. 4 is a graph depicting the effect on pigmentation of exposure of S91 cells to deoxydinucleotides $d(pA)_2$ and $d(pT)_2$ when cultured in a medium of DME plus 2% calf serum (CS). Control=no additions; 50 µM and 100 µM IBMX=isobutylmethylxanthine, 50 µM and 100 µM $d(pA)_2$=deoxyadenylic acid dinucleotide; 50 µM and 100 µM $d(pT)_2$=thymidylic acid dinucleotide.

In a fourth experiment, S91 cells were plated at a density of $20\times10^5$ cells/dish and grown for 3 days in DME plus 10% CS. On the fourth day, the medium was changed to DME plus 2% CS to slow cell proliferation. At this time, plates were either non-supplemented (controls) or given 50 µM or 100 µM IBMX, $d(pA)_2$ or $d(pT)_2$. After 3 days, the cells were collected and the melanin/cell calculated. The results are represented in FIG. 4. The cells exposed to $d(pT)_2$ showed a dose-dependent increase in melanin/cell with 50 µM $d(pT)_2$ and 100 mm $d(pT)_2$ showing a 13 and 30-fold increase respectively compared to controls. Cells exposed to $d(pA)_2$ showed a three to four-fold increase in melanin content. 100 µM IBMX gave a nearly 15-fold increase in pigmentation above the negative control, as expected.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A topical preparation for increasing pigmentation in mammalian skin, comprising DNA fragments, either single- or double-stranded, or a mixture of both, or deoxynucleotides, in an amount sufficient to increase pigmentation in mammalian skin, in a delivery vehicle.

2. The preparation of claim 1, wherein the delivery vehicle is liposomes.

3. The preparation of claim 1, further comprising diacylglycerol.

4. The preparation of claim 1, wherein the concentration of the DNA fragments is 0.05 to 10 mg/ml.

5. The preparation of claim 1, wherein the DNA fragments are dinucleotides.

6. The preparation of claim 5, wherein the concentration of the dinucleotides is 25 to 100 µM.

7. The preparation of claim 1, wherein the DNA fragments are ultraviolet-irradiated prior to commercial distribution of the preparation.

8. A topical preparation for increasing pigmentation in mammalian skin, comprising a dinucleotide selected from the group consisting of: thymidylic acid dinucleotide $(d(pT)_2)$, and deoxyadenylic acid dinucleotide $(d(pA)_2)$, in an amount sufficient to increase pigmentation in mammalian skin, in a delivery vehicle.

9. The preparation of claim 8, wherein the delivery vehicle is liposomes.

10. The preparation of claim 8, further comprising diacylglycerol.

11. The preparation of claim 8, wherein the concentration of the dinucleotides is 25 to 100 µM.

12. The preparation of claim 8, wherein the dinucleotides are ultraviolet-irradiated prior to commercial distribution of the preparation.

* * * * *